United States Patent [19]

Mahood

[11] Patent Number: 5,614,571
[45] Date of Patent: *Mar. 25, 1997

[54] STABILIZER BLEND CONTAINING PHOSPHITE

[75] Inventor: James A. Mahood, Morgantown, W. Va.

[73] Assignee: General Electric Company, Pittsfield, Mass.

[*] Notice: The term of this patent shall not extend beyond the expiration date of Pat. No. 5,500,467.

[21] Appl. No.: 361,349

[22] Filed: Dec. 21, 1994

Related U.S. Application Data

[63] Continuation-in-part of Ser. No. 307,545, Sep. 16, 1994, Pat. No. 5,424,348.
[51] Int. Cl.$^6$ ............................ C08K 5/527; C09K 15/32
[52] U.S. Cl. ...................... 252/400.24; 524/117; 524/100
[58] Field of Search ...................... 252/400.24; 524/336, 524/117, 100, 102, 103, 104, 350, 291, 236

[56] References Cited

U.S. PATENT DOCUMENTS

| | | |
|---|---|---|
| 3,039,993 | 6/1962 | Friedman . |
| 3,056,823 | 10/1962 | Hechenbleikner et al. . |
| 3,264,247 | 8/1966 | Friedman . |
| 3,281,381 | 10/1966 | Hechenbleikner et al. . |
| 3,305,520 | 2/1967 | Fritz et al. . |
| 3,305,526 | 2/1967 | Guttag . |
| 3,342,767 | 9/1967 | Buckley . . |
| 3,415,906 | 12/1968 | Shepard et al. . |
| 3,437,720 | 4/1969 | Guttag . |
| 3,441,633 | 4/1969 | Friedman . |
| 3,467,733 | 9/1969 | Dever et al. . |
| 3,482,002 | 12/1969 | Dever et al. . |
| 3,483,147 | 12/1969 | Friedman . |
| 3,488,407 | 1/1970 | Schall . |
| 3,509,091 | 4/1970 | Cleveland et al. . |
| 3,558,554 | 1/1971 | Kuriyama et al. . |
| 3,646,173 | 2/1972 | Gordon et al. . |
| 3,714,302 | 1/1973 | Dever et al. . |
| 3,794,629 | 2/1974 | Eimers et al. . |
| 3,845,168 | 10/1974 | Guttag . |
| 3,939,229 | 2/1976 | Hechenbleikner et al. . |
| 4,064,100 | 12/1977 | Hechenbleikner . |
| 4,086,304 | 4/1978 | Hutton et al. . |
| 4,187,212 | 2/1980 | Zinke et al. . |
| 4,196,117 | 4/1980 | Spivack . |
| 4,206,111 | 6/1980 | Valdiserri et al. . |
| 4,305,866 | 12/1981 | York et al. . |
| 4,318,845 | 3/1982 | Spivack et al. . |
| 4,331,585 | 5/1982 | Valdiserri et al. . |
| 4,405,739 | 9/1983 | Kinson . |
| 4,529,533 | 7/1985 | Chasar . |
| 4,708,979 | 11/1987 | Pedrazzetti et al. . |
| 4,755,546 | 7/1988 | Hechenbleikner et al. . |
| 4,782,170 | 11/1988 | Bae et al. . |
| 4,810,579 | 3/1989 | Neri et al. . |
| 4,882,374 | 11/1989 | Wang et al. . |
| 4,956,406 | 9/1990 | Myers et al. . |
| 4,957,954 | 9/1990 | Iizuka et al. . |
| 4,957,956 | 9/1990 | Neri et al. . |
| 5,124,472 | 6/1992 | Enlow . |
| 5,141,975 | 8/1992 | Enlow . |
| 5,142,083 | 8/1992 | Enlow . |

FOREIGN PATENT DOCUMENTS

| | | |
|---|---|---|
| 0392392A1 | 10/1990 | European Pat. Off. . |
| 0400454A2 | 12/1990 | European Pat. Off. . |
| 0576833A2 | 1/1994 | European Pat. Off. . |
| 0635514A1 | 1/1995 | European Pat. Off. . |
| 2944254 | 5/1980 | Germany . |
| 2087399 | 5/1982 | United Kingdom . |

Primary Examiner—Veronica P. Hoke

[57] ABSTRACT

A stabilizer blend composition is provided containing a phosphite of the formula:

$$H_3C-CH_2-CH_2-CH_2 \diagdown _{C} \diagup ^{CH_2-O} \diagdown P-O- \underset{Y^1}{\underset{|}{\bigcirc}} -Y^2$$
$$CH_3-CH_2 \diagup \quad \diagdown CH_2-O \diagup$$

(with $C(CH_3)_3$ substituent on the ring)

wherein $Y^1$ is an alkyl and $Y^2$ is tert-butyl, and an additive which is preferably a hindered phenolic, a thioester, a neutralizer, a UV stabilizer or a UV absorber. The composition in solid particle form exhibit reduced levels of dusting and are useful in polymer stabilization processes for stabilizing polymeric materials.

13 Claims, No Drawings

STABILIZER BLEND CONTAINING PHOSPHITE

This is a continuation-in-part of application(s) Ser. No. 08/307,545 filed on Sep. 16, 1994, now U.S. Pat. No. 5,424,348.

BACKGROUND OF THE INVENTION

1. Field of the Invention

The present invention relates to stabilizer blends and related polymer stabilization processes, and more particularly relates to stabilizer blends containing a phosphite and related polymer stabilization processes.

2. Description of the Related Art

Blends of phosphites and other stabilizers are generally known, and have been used for stabilizing polymer compositions. Such blends can provide the advantage of a single additive product for delivery into a polymer composition. A problem with such blends can exist for solid blend products if the components do not adequately adhere to each other resulting in particles of the blends losing their integrity and forming undesirable amounts of dust. Another problem with such blends can exist if high levels of phosphite are desired and the components, in particular the phosphite, and the other components, do not adequately adhere to each other.

Accordingly, there is a need to provide blends containing a phosphite which exhibit enhanced adhesion between the blend components.

SUMMARY OF THE INVENTION

The present invention involves stabilizer blends containing a phosphite of the formula:

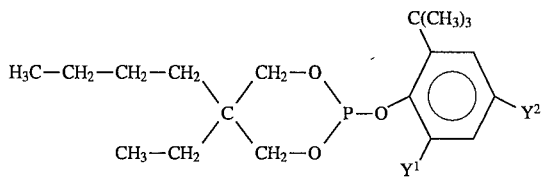

wherein $Y^1$ is an alkyl and $Y^2$ is tert-butyl. The blends are in the form of solid particles and exhibit reduced dust formation and/or allow for high loadings of phosphite due to the enhanced adhesive characteristics of the phosphite. The solid particles may be used to stabilize thermoplastic compositions.

DETAILED DESCRIPTION OF THE INVENTION

The solid stabilizer blend composition contains (a) a phosphite of the formula:

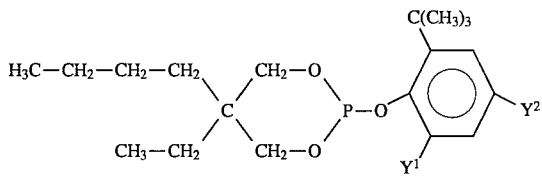

wherein $Y^1$ is an alkyl and $Y^2$ is tert-butyl, and (b) an additive component such as hindered phenols, neutralizers, hydroxylamines, thioesters and ultraviolet light stabilizers and absorbers. The phosphite is preferably present in the composition at a level of from 5 percent by weight to 95 percent by weight. The composition is preferably in the form of particles having a particle size of from 10 μm to 2 mm. The particles can be used to stabilize thermoplastic materials by addition thereto. The particles exhibit reduced levels of dust and are suitable for high loadings of phosphite.

The present invention involves a neoalkyl aryl phosphite of the formula:

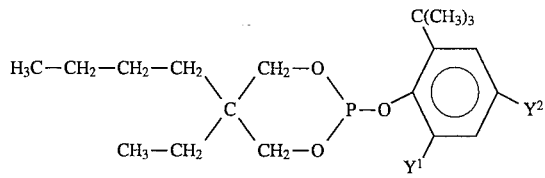

wherein $Y^1$ is independently selected from the group consisting of alkyl radicals, and preferably $Y^1$ is a tert-butyl group and $Y^2$ is a tert-butyl group.

The phosphite may be made by the reaction of 2-ethyl-2-butyl-1,3-propane diol with $PCl_3$ in the absence of a catalyst, HCl acceptor and solvent to produce an intermediate product of the formula:

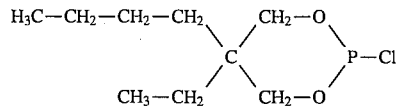

followed by the reaction with a hydroxyaryl compound of the formula:

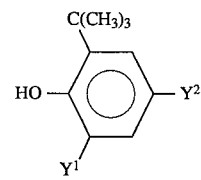

wherein $Y^1$ and $Y^2$ are as defined above. Suitable reaction methods are set out in Great Britain Patent 2087399A, U.S. Pat. No. 4,318,845 issued 1982, Spivak et al. and Article in Phosphourous & Sulfur Journal by J. D. Spivak et al. 1983, vol. 15, pp. 9–13, all of which are incorporated herein by reference.

The reaction between the diol and $PCl_3$ may be conducted in known manner, as by mixing the reactants together at room temperature, or preferably, by cooling the $PCl_3$ to a temperature between 5–15 degrees centigrade prior to addition of diol to the reactor. An excess of either reactant may be employed although it is preferred to operate with substantially stoichiometric amounts of the diol and $PCl_3$. The reaction temperature is preferably maintained between 5–15 degrees centigrade. This temperature may be readily controlled by regulating the rate of diol addition. The esterification reaction is quite exothermic in the absence of a solvent, but a temperature moderating effect is produced by the cooling effect of vigorous HCl evolution. Hence, by effective control of diol addition, the reaction may be made self-regulating in the temperature range between 5–15 degrees centigrade.

After the reaction has gone to completion, the bulk of the by-product HCl may optionally be removed by gently raising the temperature of the product to about 50 degrees centigrade and applying a vacuum.

The reaction between the intermediate product of the reaction discussed in the preceding paragraph and hydroxyaryl compound may be conducted in the same reaction vessel that was employed to produce the crude intermediate by merely introducing the hydroxyaryl compound into the reactor.

The reaction between the hydroxyaryl compound and the intermediate product in some instances may be carried out at a temperature between 35 to 100 degrees centigrade and preferably between about 45 to about 80 degrees centigrade. The pressure of the reaction system is maintained between about 50 millimeters mercury absolute to atmospheric pressure. The reaction reaches substantial completion in from 1 to about 8 hours and for practical purposes it is preferably operated under temperature and pressure conditions which will afford the maximum amount of product within 3 to about 5 hours. Although a stoichiometric excess of either reactant may be employed, it is preferred to operate with substantially stoichiometric quantities.

The hydroxyaryl compound may be any compound of the formula:

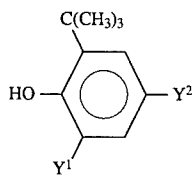

in which $Y^1$ is selected from the group consisting of alkyl groups preferably having from 1 to 8 carbon atoms, more preferably methyl or t-butyl. The reaction can be completed in the presence of a base such as an amine acceptor. Since $Y^1$ is an alkyl group, an amine acceptor should be added to help drive this reaction. If $Y^1$ is a tert-alkyl group, such as t-butyl, then a stociometeric amount of amine acceptor should be present. $Y^2$ is t-butyl, and the phosphite is a solid at room temperature.

After completion or near completion of the reaction, HCl generated during the process may readily be substantially removed by evacuating the reactor vessel. No special precautions need to be taken to remove all the HCl present, as by addition of HCl acceptor or via controlled neutralization of the acidity. The product may then be recovered by distillation, or crystallization.

The phosphites have $Y^1$ as an alkyl group such as methyl or t-butyl in order to inhibit ultraviolet light yellowing of the phosphite. If $Y^1$ is hydrogen the phosphite will have sensitivity to UV yellowing. The preferred phosphite has a phenolic degradation product boiling point of greater than 250° C., more preferably greater than 260° C. so that the volatility of the degradation product during processing of the stabilized polymer, such as polyolefins such as polypropylene which processes at 240° C. and above, is minimized. The problem of excessive volatiles can be minimized by employing an 2,4-di-butyl-6-alkyl phenyl group because such groups have corresponding 2,4-di-butyl-6-alkyl phenol degradation products which have a boiling point of greater than 260° C.

The additive component may be selected from antioxidants, ultraviolet (UV) light absorbers and UV light stabilizers, metal deactivates, phosphites (other than component) and phosphonites, peroxide scavengers, polyamide stabilizers, basic co-stabilizers (neutralizers), nucleating agent, hydroxylamines such as dialkyl aminoxy propane and more generally such as $R_2NOH$ wherein R is a $C_1$ to $C_{30}$ alkyl group such as propyl and stearyl, thioesters, and aminoxy propanote derivatives. The preferred additives are hindered phenolic antioxidants, UV absorbers, UV stabilizers and neutralizers.

Suitable additive components are selected from:
1. Antioxidants
  1.1 Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(alpha-methylcyclohexyl)-4,6 dimethylphenol, 2,6-di-octadecyl-4-methylphenol, 2,4,6,-tricyclohexyphenol, 2,6-di-tert-butyl-4-methoxymethylphenol.
  1.2 Alkylated hydroquinones, for example, 2,6-di-tert-butyl-4-methoxyphenol, 2,5-di-tert-butylhydroquinone, 2,5-di-tert-amyl-hydroquinone, 2,6-diphenyl-4octadecyloxyphenol.
  1.3 Hydroxylated thiodiphenyl ethers, for example, 2,2'-thio-bis-(6-tert-butyl-4-methylphenol), 2,2'-thio-bis-(4-octylphenol), 4,4'thio-bis-(6-tert-butyl-3-methylphenol), 4,4'-thio-bis-(6-tert-butyl-2-methylphenol).
  1.4 Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(alpha-methylcyclohexyl(phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(alpha-methylbenzyl)-4-nonylphenol), 2,2'-methylene-bis-(6-(alpha,alpha-dimethylbenzyl)-4-nonyl-phenol)- 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis(5-tert-butyl-4-hydroxy-2-methylphenol)butane. 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, di-(2-(3'-tert-butyl-2'hydroxy-5'methyl-benzyl)-6-tert-butyl-4-methylphenyl)terephthalate.
  1.5 Benzyl compounds, for example, 1,3,5-tris(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiol-terephthalate. 1,3,5-tris-(3,5-di-tert-butyl-4-hydroxybenzyl)isocyanurate. 1,3,5-tris-(4-tert-butyl-3-hydroxy-2,6-dimethylbenzyl)isocyanurate, dioctadecyl 3,5-diotert-butyl-4-hydroxybenzylphosphonate, calcium salt of monoethyl 3,5-di-tert-butyl-4-hydroxybenzylphosphonate, 1,3,5-tris-(3,5-dicyclohexyl-4-hydroxybenzyl)isocyanurate.
  1.6 Acylaminophenols, for example, 4-hydroxylauric acid anilide, 4-hydroxy-stearic acid amilide, 2,4-bis-octylmercapto-6-(3,5-tert-butyl-4-hydroxyanilino)-s-triazine, octyl-N-(3,5-di-tert-butyl-4-hydroxyphenyl)-carbamate.
  1.7 Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethylisocyanurate, thiodiethyleneglycol, di-hydroxyethyl oxalic acid diamide.
  1.8 Esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thidiethyleneglycol, dihydroxyethyl oxalic acid diamide.

1.9 Esters of beta-(5-tert-butyl-4-hydroxy-3-methylphenyl) propionic acid with mono-or polyhydric alcohols, e.g., with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

1.10 Amides of beta-(3,5-di-tert-butyl-4-hydroxyphenol)-propionic acid for example, N,N'-di-(3,5-di-tert-butyl-4-hydroxyphenylpropionyl)-hexamethylen-diamine, N,N'-di-(3,5-di-tert-butyl-4-hydroxyphenylpropionyl)trimethylenediamine, N,N'-di(3,5-di-tert-butyl-4-hydroxyphenylpropionyl)hydrazine.

2. UV absorbers and light stabilizers.

2.1 2-(2'-hydroxyphenyl)-benzotriazoles, for example, the 5'methyl-, 3'5'-di-tert-butyl-, 5'-tert-butyl-,5'(1,1,3,3-tetramethylbutyl) -,5-chloro-3', 5'-di-tert-butyl-, 5-chloro -3'tert-butyl-5'methyl -,3'sec-butyl-5'tert-butyl-,4'-octoxy,3',5'-ditert-amyl-3',5'-bis-(alpha, alpha-dimethylbenzyl)-derivatives.

2.2 2-Hydroxy-benzophenones, for example, the 4-hydroxy-4-methoxy-,4-octoxy,4-decloxy-,4-dodecyloxy-, 4-benzyloxy,4,2',4'-trihydroxy-and 2'hydroxy-4,4'-dimethoxy derivative.

2.3 Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)resorcinol, benzoylresorcinol, 2,4-di-tert-butyl-phenyl-3,5-di-tert-butyl-4-hydroxy-benzoate and hexadecyl-3,5-di-tert-butyl-4-hydroxy-benzoate.

2.4 Acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

2.5 Nickel compounds, for example, nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.

2.6 Sterically hindered amines, for example bis(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis(1,2,2,6,6,-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)piperdine; and N-(1-hydroxy-2,2,6,6-tetramethyl-piperidin-4-yl)-epsiloncaprolactam.

2.7 Oxalic acid diamides, for examples, 4,4'-dioctyloxy-oxanilide, 2,2'-di-octyloxy-5',5'-di-tertbutyloxanilide, 2,2'-di-dodecyloxy-5',5'di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of ortho-and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tris(nonylphenyl)phosphite, trilauryl phosphite, trioctadecyl phosphite, distearyl pentaerythritol diphosphite, tris(2, 4-di-tert-butylphenyl)phosphite, diisodecyl pentaerythritol diphosphite, bis(2,4-di-tert-butylphenyl)pentaerythritol diphosphite tristearyl sorbitol triphosphite, and tetrakis(2,4-di-tert-butylphenyl)-4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, Na ricinoleate and K palmitate, antimony pyrocatecholate or zinc pyrocatecholate.

8. Nucleating agents, for example, 4-tert butylbenzoic acid, adipic acid, diphenylacetic acid.

9. The present invention may also be used in conjunction with aminoxy propanoate derivatives such as methyl-3-(N, N-dibenzylaminoxy)propanoate; ethyl-3-(N,N-dibenzylaminoxy)propanonoate; 1,6-hexamethylene-bis(3-N,N-dibenzylehminoxy)propanoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

10. Suitable thio components (preferably thioesters) include 1,1,1-trimethylolethane tri(mercaptoacetate), 1,1,1-trimethylolpropane tri(mercaptoacetate), dioleyl thiodipropionate, dilauryl thiodipropionate, other thio compounds include distearyl 3,3'-thiodipropionate, dicyclohexyl -3,3'-thiodipropionate, dicetyl-3,3'-thiodipropionate, dioctyl-3,3'- thiodipropionate, dibenzyl-3,3'-thiodipropionate, laurylmyristyl-3,3'-thiodipropionate, diphenyl-3,3'-thiodipropionate, di-p-methoxyphenyl-3,3'-thiodipropionate, didecyl-3,3'-thiodipropionate, dibenzyl-3,3'-thiodipropionate, diethyl-3,3'-thiodipropionate, lauryl ester of 3-methyl-mercapto propionic acid, lauryl ester of 3-butyl-mercapto propionic acid, lauryl ester of 3lauryl-mercapto propionic acid, phenyl ester of 3-octylmercapto propionic acid, lauryl ester of 3-phenylmercapto propionic acid, lauryl ester of 3-benzylmercapto propionic acid, lauryl ester of 3-(p-methoxy) phenylmercapto propionic acid, lauryl ester of 3-cyclo-hexylmercapto propionic acid, lauryl ester of 3-hydroxy-methylmercaptopropionic acid, myristyl ester of 3-hydroxy-ethylmercapto propionic acid, octyl ester of 3-methoxy-methylmercapto propionic acid, dilauryl ester of 3-carboxyl-methylmercapto propionic acid, dilauryl ester of 3-carboxy-propylmercapto propionic acid, dilauryl-4,7-dithiasebacate, dilauryl-4,7,8,11-tetrathiotetradecandioate, dimyristyl-4,11-dithiatetradecandioate, lauryl-3-benzothiazylmercapto-propionate. Preferably the esterifying alcohol is an alkanol having 10 to 18 carbon atoms. Other esters of beta thiocarboxylic acids set forth in Gribbins U.S. Pat. No. 2,519,744 can also be used.

The blend composition preferably comprises the phosphite at a level of from 5 to 95 percent by weight based on the total weight of the composition, more preferably from 10 to 90 percent by weight thereof, and most preferably from 40 to 60 percent by weight thereof; and preferably comprises the additive component at a level of from 5 to 95 percent by weight based on the total weight of the composition, more preferably from 10 to 90 percent by weight thereof, and most preferably from 40 to 60 percent by weight thereof.

The blend composition is preferably in the form of particles having a number average diameter of between 10 μm and 2 mm, more preferably from 50 μm to 1 mm, and most preferably from 100 μm to 500 μm.

The particles are preferably made by compacting under pressure powders of the phosphite and the additive component.

The compacted particles may be added to thermoplastic composition for stabilization thereof. The particles are preferably incorporated into the thermoplastic composition at a level of from 0.01 percent by weight to 5 percent by weight based on the total weight of the composition, more preferably at a level of from 0.03 to 3 percent by weight thereof, and most preferably from 0.05 to 1 percent by weight thereof.

The preferred thermoplastics are olefin polymers. The olefin polymers contemplated herein include homopolymers and copolymers of monoolefins, preferably those monoolefins containing 1–4 carbon atoms. Illustrative examples include polyethylene (including low density, high density, ultra high molecular weight and linear low density polyethylene), polypropylene, EPDM polymers, ethylene-propylene copolymers and polyisobutylene. The stabilization of mixtures of any of these olefin polymers and copolymers likewise is contemplated.

Polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

What is claimed is:

1. A solid stabilizer composition particle comprising:
   (a) a phosphite of the formula:

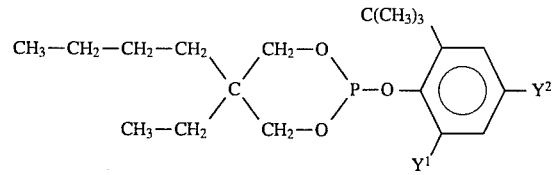

wherein $Y^1$ is alkyl and $Y^2$ is t-butyl, and
   (b) an additive selected from the group consisting of hindered phenolic antioxidants, acid neutralizers, hydroxyl amines, thioesters, ultraviolet light stabilizers and ultraviolet light absorbers.

2. The particle of claim 1 wherein said phosphite is present at a level of from 5 to 95 percent by weight based on the total weight of the particles.

3. The particle of claim 1 wherein said phosphite is present at a level of from 10 to 90 percent by weight based on the total weight of the particles.

4. The particle of claim 1 wherein said phosphite is present at a level of from 40 to 60 percent by weight based on the total weight of the particles.

5. The particle of claim 1 wherein $Y^1$ and $Y^2$ are tert-butyl.

6. A method of stabilizing a thermoplastic polymeric material comprising mixing the particle of claim 1 with the thermoplastic polymeric material.

7. The particle of claim 1 consisting of said phosphite and additive.

8. The particle of claim 1 wherein said additive is a hindered phenolic antioxidant.

9. The particle of claim 1 wherein said additive is an acid neutralizer.

10. The particle of claim 1 wherein said additive is a hydroxyl amine.

11. The particle of claim 1 wherein said additive is a thioester.

12. The particle of claim 1 wherein said additive is a hindered amine ultraviolet light stabilizer.

13. The particle of claim 1 wherein said additive is a benzophenone ultraviolet light absorber.

* * * * *